(12) United States Patent
Remmereit et al.

(10) Patent No.: US 8,741,361 B2
(45) Date of Patent: Jun. 3, 2014

(54) NGNA COMPOSITIONS AND METHODS OF USE

(71) Applicant: Life Science Nutrition AS, Hovdebygda (NO)

(72) Inventors: Jan Remmereit, Hovdebygda (NO); Ken Johnson, Stoughton, WI (US)

(73) Assignee: Life Science Nutrition AS, Hovdebygda (NO)

( * ) Notice: Subject to any disclaimer, the term of this patent is extended or adjusted under 35 U.S.C. 154(b) by 0 days.

(21) Appl. No.: 14/026,279

(22) Filed: Sep. 13, 2013

(65) Prior Publication Data

US 2014/0024607 A1    Jan. 23, 2014

Related U.S. Application Data

(63) Continuation of application No. 11/347,352, filed on Feb. 3, 2006, now Pat. No. 8,535,732, which is a continuation of application No. 11/183,721, filed on Jul. 18, 2005, now abandoned.

(60) Provisional application No. 60/589,046, filed on Jul. 19, 2004.

(51) Int. Cl.
    *A01N 65/00*    (2009.01)

(52) U.S. Cl.
    USPC .......................................................... 424/725

(58) Field of Classification Search
    None
    See application file for complete search history.

(56) References Cited

U.S. PATENT DOCUMENTS

| | | | |
|---|---|---|---|
| 5,466,547 A | 11/1995 | Khoe | 424/439 |
| 5,985,330 A | 11/1999 | Collin | |
| 6,127,113 A | 10/2000 | Atkinson et al. | |
| 6,664,050 B1 | 12/2003 | Atkinson et al. | |
| 2004/0039066 A1 | 2/2004 | Crea | 514/731 |

FOREIGN PATENT DOCUMENTS

| | | |
|---|---|---|
| JP | 402289521 | 11/1990 |
| JP | 04084872 | 3/1992 |
| JP | 05279264 | 10/1993 |
| WO | WO 00/38697 A1 | 7/2000 |
| WO | WO 01/42263 A2 | 6/2001 |

OTHER PUBLICATIONS

Mercola.com, 2 pages, Jan. 2000.
Dhurandhar, Nikhil, V.; "Infectobesity: Obesity of Infectious Origin"; The Journal of Nutrition (2001); vol. 131, No. 10, pp. 2794S-2797S.
Higa, Herman H. et al.; "Influenza Virus Hemagglutinins Differentiate between Receptor Determinants Bearing N-Acetyl-,N-Glycolyl-, and N,O-Diacetyineuraminic Acids"; Virology (Jul. 15, 1985); vol. 144, No. 1, pp. 279-282.
Suzuki, Takashi, et al.; "Receptor Specificities of Human Respiroviruses"; Journal of Virology (May 2001); vol. 75, No. 10, pp. 4604-4613.
Crocker, Paul R., et al.; "Siglecs, sialic acids and innate immunity"; Trends in Immunology (Jun. 1, 2001); vol. 22, No. 6., pp. 337-342.
Suzuki, Takashi, et al.; "Swine influenza virus strains recognize sialylsugar chains containing the molecular species of sialic acid predominantly present in the swine tracheal epithelium"; FEBS Letters (Jan. 1, 1997); vol. 404, pp. 192-196.
Tangvoranuntakul, Pam, et al.; "Human uptake and incorpration of an immunogenic nonhuman dietary sialic acid"; Proceedings of the National Academy of Sciences of USA (Oct. 14, 2003); vol. 100, No. 21, pp. 12045-1205.
Brinkman-Van Der Linden, Els C.M., et al.; "Loss of N-Glycolylneuraminic Acid in Human Evolution—Implications for Sialic Acid Recognition by Siglecs"; The Journal of Biological Chemistry (Mar. 24, 2005); vol. 275, No. 12, pp. 8633-8640.
Varki, Ajit; "N-glycolylneuraminic acid deficiency in humans"; Biochimie (Jul. 1, 2001); vol. 83, No. 7, pp. 615-622.
Malykh, Yanina N., et al.; "N-Glycolyineuraminic acid in human tumors"; Biochimie (Jul. 1, 2001); vol. 83, No. 7, pp. 623-634.
Vangipuran, Sharada D., et al.; Abstract: "A Human Adenovirus Enhances Preadipocyte Differentiation"; Obesity Research; http://www.obesityresearch.org/cgi/content/abstract/12/5/770; (1 pg.).
Nicolson, Garth L.; "Considerations when Uundergoing Treatment for Gulf War Illness/CFS/FMS/Rheumatoid Arthritis"; Intern J. Medicine 1998; 1: 123-128; http://64.233.167.104/search?q=cache; VleCWtuvOesJ:www.immed.org/publications/treatment_cons: (9 pgs.).
Dhurandhar, Nikhil V., et al.; "Human Adenovirus Ad-36 Promotes Weight Gain in Male Rhesus and Marmoset Monkeys"; Nutritional Immunology; 1) Experimental Biology '99 Apr. 1999, Washington DC; 2) The European Congress on Obesity, May 2000, Vienna, Austria, American Society for Nutritional Sciences 2002; pp. 3155-3160.

*Primary Examiner* — Michael Meller
(74) *Attorney, Agent, or Firm* — Casimir Jones SC

(57) ABSTRACT

The present invention relates to the field of viral disorders, and in particular to viral obesity. Compositions comprising nutraceutical agents are provided for treating viral obesity. Additionally, compositions comprising nutraceutical agents targeting adenoviruses are provided.

1 Claim, 2 Drawing Sheets

Weight

How was your workout today?

How do you feel?

Do you have a cold 0, or are you healthy 9?

Do you feel the drink helps you?

How is workout energy and joy?

Do you like the sport drink?

NGNA COMPOSITIONS AND METHODS OF USE

CROSS-REFERENCE TO RELATED APPLICATIONS

This application is a continuation of allowed U.S. patent application Ser. No. 11/347,352, filed Feb. 3, 2006, which will issue on Sep. 17, 2013 as U.S. Pat. No. 8,535,732, which is a continuation of abandoned U.S. patent application Ser. No. 11/183,721, filed Jul. 18, 2005, which claims the benefit of U.S. Provisional Patent Application 60/589,046, filed Jul. 19, 2004.

FIELD OF THE INVENTION

The present invention relates to the field of nutraceuticals, and in particular to nutraceuticals comprising n-glycolylneuraminic acid (NGNA). Compositions comprising NGNA find use in inducing physiological responses such as alleviating the symptoms of viral-induced obesity, alleviating the symptoms of colds, preventing the onset of colds, increasing energy and increasing the feeling of well-being in subjects.

BACKGROUND OF THE INVENTION

Obesity is a prevalent nutritional disorder in the United States. Obesity in childhood, adolescence, and adulthood represents a serious concern and a challenge to the medical and lay communities. Major impacts include effects on blood pressure, intermediary metabolism, respiratory function, psychological well-being, social adaptation, and educational performance. Obesity is associated with significant adult morbidity, including long-term effects on cardiovascular health and premature mortality.

Accumulation of excess fat mass occurs when total energy intake exceeds total energy expenditure, including the energy allowance for normal growth. This energy imbalance can result from excessive energy intake and/or reduced energy expenditure for body metabolism, thermoregulation, and physical activity. Increases in energy intake are observed in genetic syndromes, such as Prader-Willi syndrome, Cushing syndrome, and drug-induced obesity. Reductions in energy expenditure characterize hormonal deficiency states, including hypothyroidism and growth hormone deficiency.

The etiology of obesity is considered to be multifactorial. Animal obesity has been classified into nine different groups, including obesity of neural, endocrine, pharmacological, nutritional, environmental, seasonal, genetic, idiopathic or of viral origin (see, e.g., Sclaffini, A. (1984) Int. J. Obesity 8: 491-508; herein incorporated by reference in its entirety). While genetic and behavioral components of obesity have been the focus of intense study, six pathogens have been reported to cause obesity in animal models (see, e.g., Atkinson R. L., et al., (1997) Int. J. of Obesity 21:S36; Carter J. K., et al., (1983) Infect. Immun. 39:410-422; Carter J. K., et al., (1983) Avian Dis 27:317-322; Dhurandhar N. V., et al., (1990) J. Bombay Vet. College 2:131-132; Dhurandhar N. V., et al., (1992) Vet. Microbiol. 31:101-107; Dhurandhar N. V., et al., (1996) Obesity Res 4:24S; Dhurandhar N. V., et al., (2000) Int. J. Obesity 24:989-996; Gosztonyi G., et al., (1995) Current Topics in Microbiol. Immunol. 190:39-73; Lyons M. J., et al., (1982) Science 216:82-85; each herein incorporated by reference in their entireties). Indeed, the human adenovirus Ad-36 is implicated in causing obesity in humans (see, e.g., Atkinson R. L., et al., (1998) Int. J. Obesity 22:S57; Dhurandhar N. V., et al., (1997) FASEB J 3:A230; each herein incorporated by reference in their entireties).

Treatment options for virally induced obesity is limited to traditional approaches (e.g., diet management, exercise management, lifestyle management, surgery, and anorectic agents (e.g., phentermine, phenylpropanolamine, mazindol, ephedra, and sibutramine)). What is needed are improved methods of treating viral obesity.

SUMMARY OF THE INVENTION

The present invention relates to the field of nutraceuticals, and in particular to nutraceuticals comprising n-glycolylneuraminic acid (NGNA). Compositions comprising NGNA find use in inducing physiological responses such as alleviating the symptoms of viral-induced obesity, alleviating the symptoms of colds, preventing the onset of colds, increasing energy and increasing the feeling of well-being in subjects.

In certain embodiments, the present invention provides a composition for treating symptoms of viral induced obesity comprising a dietary supplement in an amount effective for alleviating symptoms of viral induced obesity. In preferred embodiments, the dietary supplement agent is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*. In other preferred embodiments, the composition further comprises an excipient.

In preferred embodiments, the present invention provides a food product comprising the composition.

In other preferred embodiments, the present invention provides the composition further comprising an additional source of calories. In still other preferred embodiments, the composition is beverage, bar, powder, or shake. In yet other preferred embodiments, the composition forms parts of weight loss diet regimen. In still other preferred embodiments, the source comprises a fat source. In yet other preferred embodiments, the composition comprises a fiber source. In still other preferred embodiments, the composition comprises a protein source.

In preferred embodiments, the composition is formulated for oral administration. In other preferred embodiments, the composition is formulated as a tablet. In still other preferred embodiments, the composition is formulated as a capsule. In yet other preferred embodiments, the composition further comprises a foodstuff.

In certain embodiments, the present invention provides a composition for treating infection by a virus known to cause viral obesity comprising a dietary supplement in an amount effective to inhibit the infection. In preferred embodiments, the dietary supplement agent is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*. In preferred embodiments, the composition further comprises an excipient.

In preferred embodiments, the composition is formulated for oral administration. In other preferred embodiments, the composition is formulated as a tablet. In still other preferred embodiments, the composition is formulated as a capsule. In yet other preferred embodiments, the composition further comprises a foodstuff.

In certain embodiments, the present invention provides a method of treating symptoms associated with viral induced obesity comprising providing a subject and at least one dietary supplement, and administering the dietary supplement to the patient under conditions such that the symptoms associated with viral induced obesity are alleviated. In certain embodiments, the dietary supplement is an anti-viral agent. In other preferred embodiments, the dietary supplement is NGNA. In yet other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*.

In preferred embodiments, the symptom being treated is weight gain. In preferred embodiments, the alleviation is weight loss. In other preferred embodiments, the symptom is obesity. In preferred embodiments, the dietary supplement is administered orally.

In preferred embodiments, the method further comprises administering an antibiotic. In other preferred embodiments, the method further comprises administering an antiviral pharmaceutical agent. In still other preferred embodiments, the method further comprises administering an anorectic agent. In preferred embodiments, the administration of the dietary supplement induces weight reduction in a subject.

In certain embodiments, the present invention provides a method of treating infection by a virus that causes viral obesity comprising providing a subject and at least one dietary supplement, and administering the dietary supplement to the patient under conditions such that the infection is inhibited. In preferred embodiments, the dietary supplement is an anti-viral agent. In other preferred embodiments, the dietary supplement is NGNA. In yet other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*.

In preferred embodiments, the virus is Ad-36 or SMAM-1. In preferred embodiments, the dietary supplement is administered orally. In preferred embodiments, the method further comprises administering an antibiotic. In other preferred embodiments, the method further comprises administering an antiviral pharmaceutical agent. In still other preferred embodiments, the method further comprises administering an anorectic agent. In preferred embodiments, the administration of the dietary supplement induces weight reduction in a subject.

In certain embodiments, the present invention provides a method of preventing viral related obesity comprising providing a subject and at least one dietary supplement and administering the dietary supplement to the subject under conditions such that susceptibility to infection by Ad-36 or SMAM-1. In preferred embodiments, the dietary supplement is an anti-viral agent. In other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*. In still other preferred embodiments, the symptom is weight gain. In preferred embodiments, the symptom being treated is obesity. In other preferred embodiments, the symptom is infection by adenovirus Ad-36 or SMAM-1.

In preferred embodiments, the dietary supplement is administered orally. In other preferred embodiments, the method further comprises administering an antibiotic. In still other preferred embodiments, the method further comprises administering an antiviral pharmaceutical agent. In yet other preferred embodiments, the method further comprises administering an anorectic agent. In preferred embodiments, the administration of the dietary supplement induces weight reduction in a subject.

In certain embodiments, the present invention provides a method of treating a subject suspected of having an infection by a virus that causes viral obesity or that has symptoms caused by viral induced obesity comprising providing a subject suspected of having an infection by a virus that causes viral obesity or that has symptoms caused by viral induced obesity and at least one dietary supplement, wherein the subject is following a dietary, wherein the subject is following a weight loss diet regimen, and a composition comprising a dietary supplement in an amount effective for alleviating symptoms of viral induced obesity; and administering the composition to the subject. In preferred embodiments, the dietary supplement is an anti-viral agent. In other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*. In preferred embodiments, the symptom being treated is weight gain. In other preferred embodiments, the symptom being treated is obesity. In yet other preferred embodiments, the symptom being treated is infection by adenovirus Ad-36 or SMAM-1.

In preferred embodiments, the dietary supplement is administered orally. In other preferred embodiments, the method further comprises administering an antibiotic. In still other preferred embodiments, the method further comprises administering an antiviral pharmaceutical agent. In yet other preferred embodiments, the method further comprises administering an anorectic agent. In preferred embodiments, the administration of the dietary supplement induces weight reduction in a subject.

In certain embodiments, the present invention provides a method of treating a subject suspected of having an infection by a virus that causes viral obesity or that has symptoms caused by viral induced obesity comprising providing a subject suspected of having an infection by a virus that causes viral obesity or that has symptoms caused by viral induced obesity and a composition comprising a dietary supplement in an amount effective for alleviating symptoms of viral induced obesity and an additional source of calories; and administering the composition to the subject. In preferred embodiments, the dietary supplement is an anti-viral agent. In other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*.

In preferred embodiments, the symptom being treated is weight gain. In other preferred embodiments, the symptom is obesity. In still other preferred embodiments, the symptom is infection by adenovirus Ad-36 or SMAM-1. In preferred embodiments, the nutraceutical agent is administered orally.

In preferred embodiments, the method further comprises administering an antibiotic. In other preferred embodiments, the method further comprises administering an antiviral pharmaceutical agent. In still other preferred embodiments, the method further comprises administering an anorectic agent. In preferred embodiments, the administration of the dietary supplement induces weight reduction in a subject.

In preferred embodiments, the present invention provides a method of maintaining weight reduction in a subject having an infection by a virus that causes viral obesity or that has symptoms caused by viral induced obesity comprising providing a subject having an infection by a virus that causes viral obesity or that has symptoms caused by viral induced obesity and a composition comprising a dietary supplement in an amount effective for alleviating symptoms of viral induced; and administering the composition to the subject. In preferred embodiments, the dietary supplement is an antiviral agent. In other preferred embodiments, the dietary supplement is selected from the group consisting of catechins, flavenoids, *Echinacea*, cascara, n-glycolylneuraminic acid, soy/red clover, rosemary/lemon balm, selenite, barley grass, lauric acid, and *Phyllanthus amarus/niruri*.

In preferred embodiments, the symptom being treated is weight gain. In other preferred embodiments, the symptom is obesity. In still other preferred embodiments, the symptom is infection by adenovirus Ad-36 or SMAM-1. In preferred embodiments, the nutraceutical agent is administered orally.

In preferred embodiments, the method further comprises administering an antibiotic. In other preferred embodiments, the method further comprises administering an antiviral pharmaceutical agent. In still other preferred embodiments, the method further comprises administering an anorectic agent. In preferred embodiments, the administration of the dietary supplement induces weight reduction in a subject.

In further embodiments, the present invention provides compositions for inducing a physiological effect selected from the group consisting of alleviation of the symptoms of viral induced obesity, increasing energy, increasing the feeling of well-being and alleviation of cold symptoms, said composition comprising a n-glycolylneuraminic acid in an amount effective for inducing said physiological effect. In some embodiments, the composition further comprises an agent selected from the group consisting of catechins, flavenoids, *Echinacea*, cascara, soy/red clover, rosemary/lemon balm, selenite, barley grass, lauric acid, and *Phyllanthus amarus/niruri*. In some embodiments, the composition further comprises an excipient. In further embodiments, the composition is formulated for oral administration. In still further embodiments, the composition is formulated as a tablet. In still other embodiments, the composition is formulated as a capsule. In some embodiments, the compositions comprise a foodstuff. In some embodiments, the composition is provided as part of a nutritional supplement, while in other embodiments, the composition is provided as a dietary supplement.

In some embodiments, the present invention provides methods of inducing a physiological effect selected from the group consisting of alleviation of the symptoms of viral induced obesity, increasing energy, increasing the feeling of well-being and alleviation of cold symptoms in a subject comprising: providing a composition comprising n-glycolylneuraminic, and administering said composition to said patient under conditions such that said physiological effect is induced. In some embodiments, the composition further comprises an agent selected from the group consisting of catechins, flavenoids, *Echinacea*, cascara, soy/red clover, rosemary/lemon balm, selenite, barley grass, lauric acid, and *Phyllanthus amarus/niruri*. In some embodiments, the symptom of viral induced obesity is weight gain. In some embodiments, alleviation of the symptoms of viral induced obesity is weight loss. In some embodiments, the symptom is obesity. In some embodiments, the composition is administered orally. In some embodiments, the methods further comprise administering an antibiotic. In some embodiments, the methods further comprise administering an antiviral pharmaceutical agent. In some embodiments, the methods further comprise administering an anorectic agent. In some embodiments, the administration of the composition induces weight reduction in a subject. In some embodiments, the composition is a dietary supplement. In some embodiments, the composition is a nutritional supplement. In some embodiments, the composition is provided in a food or a drink.

DESCRIPTION OF THE FIGURES

FIG. 2a—How was your workout today?; FIG. 2b—How do you feel?; FIG. 2c: Do you have a cold 0, or are you healthy 9?; FIG. 2d: Do you feel the drink helps you? FIG. 2e—How is workout energy and joy?; and FIG. 2F—Do you like the sport drink?. The test subject were asked to rate their responses to these questions on a scale of)–9, 9 being the most positive.

DEFINITIONS

Figure 1A:
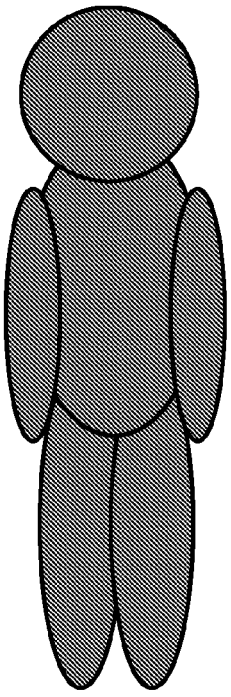
FIG. 1a provides a chart showing body composition before (Før) and after (etter) the eight week NGNA sport drink study.

As used herein, the term "obesity" and related terms refers to an increase in body weight beyond the limitation of skeletal and physical requirement, as the result of an excessive accumulation of fat in the body.

As used herein, the term "anorectic agent" and related terms refer to pharmaceutical agents used to induce weight loss in a subject. Examples of anorectic agents include, but are not limited to, phentermine, phenylpropanolaminea, mazindol, ephedra, and sibutramine.

As used herein, the term "phytonutrient" refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

As used herein, the term "functional foods" refers to food products that include biologically active nutraceutical agents.

As used herein, the terms "nutraceutical agent," and related terms, refer to natural, bioactive chemical compounds that have health promoting, disease preventing or medicinal properties. Examples of nutraceutical agents include, but are not limited to, *Allium Cepa, Allium Sativum, Aloe Vera, Angelica* Species, Naturally Occurring Antioxidants, *Aspergillus Oryzae* Enzyme Therapy, barley grass, Bromelain, Carnitine, Carotenoids and Flavonoids, Catechin, *Centella Asiatica* (*Gotu kola*), Coenzyme Q10, Chinese Prepared Medicines, *Coleus Forskohlii, Commiphora Mukul, Crataegus Oxyacantha* (Hawthorne), *Curcuma Longa* (Turmeric), *Echinacea* Species (Purple Coneflower), *Eleutherococcus Senticosus* (*Siberian Ginseng*), *Ephedra* Species, Dietary Fish Oil Consumption and Fish Oil Supplementation, *Genistein, Ginkgo Biloba, Glycyrrhiza* (Licorice), *Hypericum Perforatum* (St. John's Wort), *Hydrastis* (Goldenseal) and Other Berberine-Containing Plants, *Lactobacillus, Lobelia* (Indian Tobacco), *Melaleuca Alternifolia, Mentha Piperita*, NGNA, *Panax Ginseng*, Pancreatic Enzymes, *Piper Mythisticum, Procyanidolic Oligomers, Pygeum Africanum, Quercetin, Sarsaparilla* Species, *Serenoa Repens* (Saw palmetto, Sabal serrulata), *Silybum Marianum* (Milk Thistle), Rosemary/Lemon balm, Selenite, *Tabebuia Avellanedae* (LaPacho), *Taraxacum Officinale, Tanacetum Parthenium* (Feverfew), Taxol, *Uva Ursi* (Bearberry), *Vaccinium Myrtillus* (Blueberry), *Valerian Officinalis, Viscum Album* (Mistletoe), Vitamin A, Beta-Carotene and Other Carotenoids, and *Zingiber Officinale*(Ginger).

As used herein, the term "weight loss diet regimen" or related terms, is used broadly to include any type of weight loss plan used by a subject. Examples of weight loss diet regimens include, but are not limited to, Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, Zone diet, running, swimming, meditation, yoga, hypnosis, clinical therapy, bicycling, walking, hypnosis, rehabilitory training, a dietary plan provided through a dietician, and surgical procedures.

As used herein, the terms "subject" and "patient" refer to any animal, such as a mammal like a dog, cat, bird, livestock, and preferably a human. Specific examples of "subjects" and "patients" include, but are not limited to, individuals suffering from viral obesity.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

The present invention relates to the field of nutraceuticals, and in particular to nutraceuticals comprising n-glycolylneuraminic acid (NGNA). Compositions comprising NGNA find use in inducing physiological responses such as alleviating the symptoms of viral-induced obesity, alleviating the symptoms of colds, preventing the onset of colds, increasing energy and increasing the feeling of well-being in subjects.

A. Viral Obesity

In the U.S., the prevalence of obesity increased by 30% from 1980 to 1990, and this increase appears to be continuing. One etiology of human obesity is of infectious origin (see, e.g., Dhurandhar, N. (2001) J. Nutr. 131: 2794S-2797S; herein incorporated by reference in its entirety). Six pathogens are reported to cause obesity in animals. Canine distemper virus was the first virus reported to cause obesity in mice (see e.g., Lyons M., et al., (1982) Science 216:82-85; Bernard A., et al., (1988) Comp. Biochem. Physiol. 91B:691-696; Bernard A., et al., (1991) Virology 313:545-551; Bernard A., et al., (1993) J. Neuropath. Exp. Neuro. 52:471-480; McFerran J., et al., (1975) Am. J. Vet. Res. 36:527-534; Bernard A., et al., (1999) J. Virology 73(9):7317-7327; each herein incorporated by reference in their entireties), followed by the avian retrovirus Rous-associated virus-7 shown to cause stunting, obesity and hyperlipidemia in chickens (see e.g., Carter J. K., et al., (1983) Infect. Immun. 39:410-422; Carter J. K., et al., (1983) Avian Dis 27:317-322; each herein incorporated by reference in their entireties). The obesity-promoting effect of Borna disease virus has been demonstrated in rats (see e.g., Gosztonyi G. & Ludwig H. (1995) Current Topics in Microbiol. Immunol. 190:39-73; Fabricant C. G., et al., (1983) Federation Proc 42:2476-2479; each herein incorporated by reference in their entireties). Scrapie agents were reported to induce obesity in mice and hamsters (see e.g., Kim Y. S., et al., (1987) J. Infect. Dis. Aug; 156(2):402-405; Carp R. L., et al., (1990) J. Infect. Dis. 161(3):462-466; Carp R. L., et al., (1998) J. Gen. Virol. 79(Pt 11):2863-2869; Kim Y. S., et al., Proc. Soc. Exp. Biol. Med. 189(1):21-27; each herein incorporated by reference in their entireties). The final two reports were of SMAM-1, an avian adenovirus (see e.g., Dhurandhar N. V., et al., (1990) J. Bombay Vet. College 2:131-132; Dhurandhar N. V., et al., (1992) Vet. Microbiol. 31:101-107; Ajinkya S. M. (1985) Final Technical Report, ICAR 1985: 13-43 Red and Blue Cross Publishing Bombay, India; each herein incorporated by reference in their entireties), and Ad-36 (see e.g., Dhurandhar N. V., et al., (2000) Int. J. Obesity 24:989-996; Dhurandhar N. V., et al., (2001) Int. J. Obesity 25:990-996; Kolesar J. M., et al., (2000) J. Chromatog. B. 744:1-8; herein incorporated by reference in its entirety), a human adenovirus that caused obesity in animals. Additionally, an association with human obesity is the unique feature of SMAM-1 (see, e.g., Dhurandhar N. V., et al., (1997) Obesity Res 5:464-469; herein incorporated by reference in its entirety) and Ad-36 (see, e.g., Vangipuram, S. D., et al., (2004) Obesity Research 12:770-777; Dhurandhar, N. V., et al., (2002) J. Nutr. 132:3155-3160; Atkinson R. L., et al., (1998) Int. J. Obesity 22:S57; Dhurandhar N. V., et al. (1997) FASEB J 3:A230; Atkinson R. L., et al., (2000) Int. J. Obesity suppl 1:S39; Dhurandhar N. V., et al.; (1999) FASEB J 13(4): A369; each herein incorporated by reference in their entireties).

U.S. Pat. Nos. 6,127,113 and 6,664,050, each herein incorporated by reference in their entireties, characterize Ad-36 induced viral obesity. In particular, humans who suffer from viral obesity (i.e., obesity caused by a virus) have, on the average, significantly lower triglycerides (TG), cholesterol (CHOL) and low-density-lipoprotein-associated cholesterol (LDL-CHOL) levels than persons who suffer from obesity that is not viral. In fact, the average TG, CHOL and LDL-CHOL levels of persons with viral obesity are within the normal ranges for persons who are not obese. Diagnostic and screening approaches for Ad-36 and Ad-36p are provided. Anti-obesity vaccines, wherein inactivated viral nucleic acid (e.g., Ad-36 nucleic acid) is administered to a subject, are also described.

B. Dietary Supplements

The present invention provides dietary supplements comprising nutraceutical agents. Nutraceutical agents are natural, bioactive chemical compounds that have health promoting, disease preventing or medicinal properties. Examples of nutraceuticals include, but are not limited to, *Allium Cepa, Allium Sativum, Aloe Vera, Angelica* Species, Naturally Occurring Antioxidants, *Aspergillus Oryzae* Enzyme Therapy, barley grass, Bromelain, Carnitine, Carotenoids and Flavonoids, Catechin, *Centella Asiatica (Gotu kola)*, Coenzyme Q10, Chinese Prepared Medicines, *Coleus Forskohlii, Commiphora Mukul*, Conjugated Linoleic Acids (CLAs), *Crataegus Oxyacantha* (Hawthorne), Curcuma Longa (Turmeric), *Echinacea* Species (Purple Coneflower), *Eleutherococcus Senticosus (Siberian Ginseng)*, *Ephedra* Species, Dietary Fish Oil Consumption and Fish Oil Supplementation, Genistein, *Ginkgo Biloba, Glycyrrhiza* (Licorice), *Hypericum Perforatum* (St. John's Wort), *Hydrastis* (Goldenseal) and Other Berberine-Containing Plants, *Lactobacillus, Lobelia* (Indian Tobacco), *Melaleuca Alternifolia, Menaquinone, Mentha Piperita*, n-glycolylneuraminic acid (NGNA), *Panax Ginseng*, Pancreatic Enzymes, *Piper Mythisticum, Procyanidolic Oligomers, Pygeum Africanum, Quercetin, Sarsaparilla* Species, Serenoa Repens (*Saw palmetto, Sabal serrulata*), *Silybum Marianum* (Milk Thistle), Rosemary/Lemon balm, *Selenite, Tabebuia Avellanedae* (LaPacho), *Taraxacum Officinale, Tanacetum Parthenium* (Feverfew), *Taxol, Uva Ursi* (Bearberry), *Vaccinium Myrtillus* (Blueberry), *Valerian Officinalis, Viscum Album* (Mistletoe), Vitamin A, Beta-Carotene and Other Carotenoids, and *Zingiber Officinale* (Ginger).

Several nutraceutical agents are used in treating viral disorders (e.g., Genistein (in soy/red clover), rosemary/lemon balm, selenite, barley grass, lauric acid, *Phyllanthus amarus/niruri* (see, e.g., Nicolson, G. (1998) J. Medicine 1:123-128; herein incorporated by reference in its entirety). Additional anti viral nutraceutical agents include, but are not limited to, catechins, flavenoids, *Echinacea*, cascara, and NGNA. Preferably, NGNA is provided from sea cucumbers, e.g., an extract of sea cucumbers, or is prepared from chitin. In some embodiments, NGNA is prepared as described in WO 00/38967, incorporated by reference herein its entirety. For example, N-glycolylneuraminic acid can be purchased commercially from, for example, Sigma Chemical Company, St. Louis, Mo. N-glycolylneuraminic acid also can be synthesized. For example, CMP-N-acetylneuraminic acid hydroxylase can be used to synthesize N-glycolylneurarninic acid as its CMP-glycoside. See, Schlenzka et al., Glycobiolog, 1994, 4(5):675-683. Non-enzymatic methods of synthesis include, for example, synthesis from N-acetylneuraminic acid using methanol or hydrochloric acid and benzylalcohol. Other synthesis methods are described in Choi et al., J. Org. Chem., 1996, 61:8/39 (from mannosamine), Faillard et al., J. Physiol. Chem.' 1965, 344:167 (from glucosamine), U.S. Pat. Nos. 4,774,326 and 4,774,327, both of which are incorporated by reference herein in their entirety.

In preferred embodiments, the present invention provides compositions comprising dietary supplements (e.g., NGNA) for inducing physiological responses such as alleviating the symptoms of viral-induced obesity, alleviating the symptoms of colds, preventing the onset of colds, increasing energy and increasing the feeling of well-being in subjects. Such compositions may contain, for example, between 0.1 g and 10.0 g of dietary supplements (e.g., NGNA), preferably between 0.5 g and 2.0 g of dietary supplements (e.g., NGNA), and even more preferably, approximately 1.0 g of dietary supplements (e.g., NGNA). Furthermore, dietary supplements (e.g., NGNA) are preferably provided in an amount sufficient to induce the physiological response desired (e.g., alleviation of the symptoms of viral-induced obesity, alleviation of the symptoms of colds, prevention of the onset of colds, increasing energy and increasing the feeling of well-being in subjects). In some embodiments, the compositions are provided for use in inducing one of the foregoing responses, while in other embodiments, the compositions are provided for use in inducing two or more of the foregoing responses.

The present invention further provides methods for treating the physiological conditions discussed above (e.g., conditions such as obesity, periodic weight gain, lack of energy, mild depression, colds, etc.). In preferred embodiments, dietary supplements are used in treating viral induced obesity. In other preferred embodiments, dietary supplements are used in treating infection caused by a virus that causes viral obesity (e.g., Ad-36). In other preferred embodiments, dietary supplements are used in preventing viral related obesity through targeting of viruses that cause viral obesity (e.g., Ad-36, Ad-36p, SMAM-1). In some embodiments, the compositions are provided for use in treating one of the foregoing conditions, while in other embodiments, the compositions are provided for use in treating two or more of the foregoing conditions.

The dietary supplements of the present invention are further used in conjunction with a weight loss diet regimen. The present invention is not limited to a particular kind of weight loss diet regimen (e.g., exercise, reduced calorie intake, etc.). In preferred embodiments, the weight loss diet regimen is a dietary plan (e.g., Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, and Zone diet. In still other preferred embodiments, the weight loss diet regimen is an exercise plan (e.g., running, swimming, meditation, yoga, hypnosis, clinical therapy, bicycling, walking, etc.). In still other preferred embodiments, the weight loss diet regimen is a clinically assisted plan (e.g., hypnosis, rehability training, a dietary plan provided through a dietician, surgical procedures, etc.).

The dietary supplements of the present invention may further be administered in any form (e.g., pill, food product, etc.). In preferred embodiments, the dietary supplements are provided as a beverage, bar, powder, pill, or shake (e.g., a nutritional supplement as described in more detail below).

The dietary supplements of the present invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., approximately 1 g of a nutraceutical agent) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals. In preferred embodiments, a dietary supplement increases satiety and results in a decrease in caloric intake and subsequent weight loss. In particularly preferred embodiments, a dietary supplement regulates viruses (e.g., adenoviruses).

III. Delivery of Dietary Supplements

Dietary supplements of the present invention may be delivered in any suitable format. In preferred embodiments, dietary supplements are formulated for oral delivery.

The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

B. Nutritional Supplements

In other embodiments, the present invention provides nutritional supplements (e.g., energy bars or meal replacement bars or beverages) comprising a nutraceutical agents. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate;

sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono-and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the nutritional supplement preferably contain between 0.1 g and 10.0 g of a nutraceutical agent, preferably between 0.5 and 2.0 g a nutraceutical agent, and even more preferably approximately 1.0 g a nutraceutical agent. It is understood by those of skill in the art that other ingredients can be added to those described herein, for example, fillers, emulsifiers, preservatives, etc. for the processing or manufacture of a nutritional supplement.

C. Food Products

In still further embodiments, the present invention provides functional foods, including food products, prepared food products, or foodstuffs comprising nutraceutical agents. For example, in some embodiments, beverages and solid or semi-solid foods comprising nutraceutical agents are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

Servings of the food product preferably contain between 0.1 g and 10.0 g of a nutraceutical agent, preferably between 0.5 and 2.0 g of a nutraceutical agent, and even more preferably approximately 1.0 g of a nutraceutical agent.

EXAMPLES

Example 1

A sports drink containing NGNA was formulated for use by humans. The NGNA was made from glucosamine residues derived from crab chitin. The finished drink (per 500 ml bottle) contained: pure water; 1% Glycerol/(0.1-10%); lemon flavor; potassium sorbate/sodium benzoate as stabilizers; and 2 mg of 99% pure NGNA.

Example 2

Figure 1B:
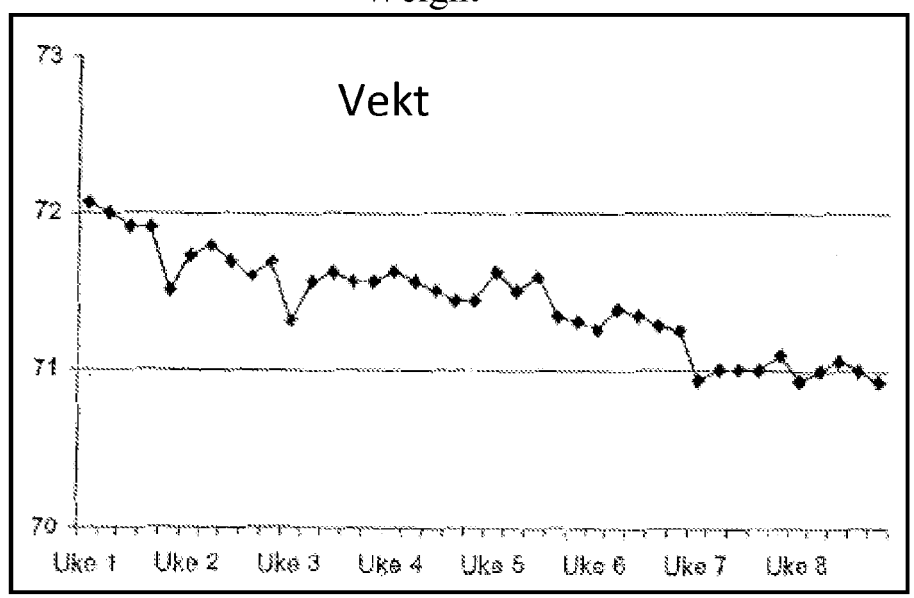
FIG. 1b is a graph showing a decrease in average weight of the subjects involved in the study.
Figure 2A:
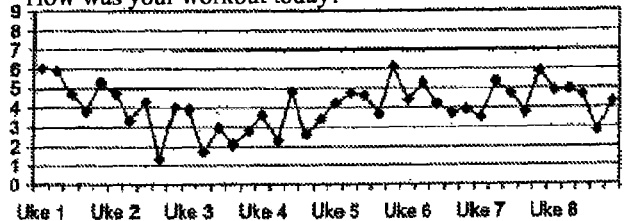
FIGS. 2a-f provide graph of responses over the eight week (Uke) period of the NGNA sport drink study to the following questions.
Figure 2B:
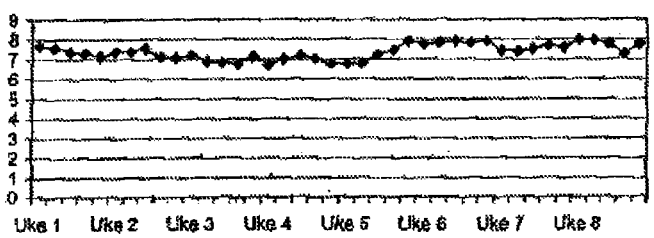
Figure 2C:
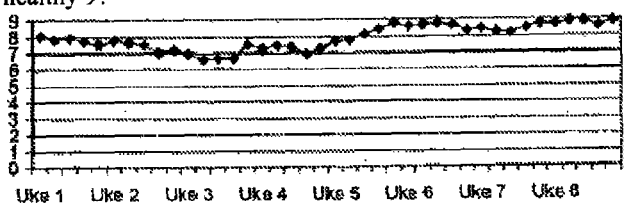
Figure 2D:
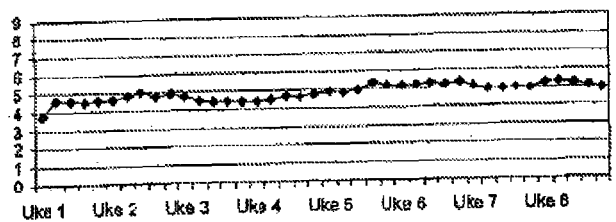
Figure 2E:
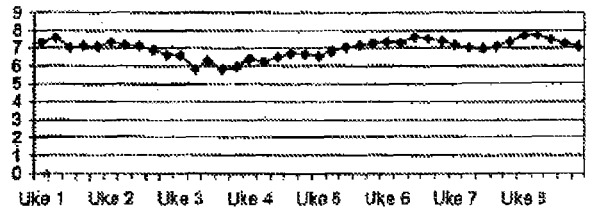
Figure 2F:
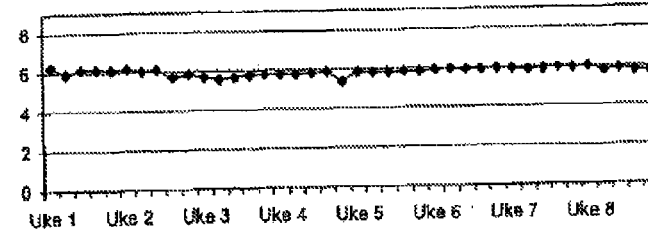

The sports drink described in Example 1 was tested in a group of 18 subjects. The subjects were supplied one 500 ml bottle of the sport drink containing 2 mg NGNA. The drink was administered during exercise or during the day when not exercising over an eight week period. The subjects worked out an average of about four times per week. The following measurements were taken during the study: fett/fat %, vekt/weight, overarm/upper arm in cm, midje/waist in cm, lår/thighs in cm. These results are summarized in FIG. 1A. As can be seen, there was a steady decrease in weight during the study (FIG. 1B). The subjects were also asked to evaluate other physiological effects of the drink. The subjects were asked to rank the impact of the drink on a scale of 0 to 9 (with 9 being a positive impact) with respect to the following questions:

a. How was your workout today
b. How do you feel?
c. Do you have a cold 0, or are you healthy 9?
d. Do you feel the drink helps you?
e. How is workout energy and joy?
f. Do you like the sport drink?

The results are presented in FIGS. 2a-f, respectively. As can be seen, there were positive responses for well-being, colds, and energy/workout joy.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for treating obesity in a human in need thereof consisting essentially of administering to said human in need thereof a therapeutically effective amount of a mixture of sea cucumber extract and an extract selected from the group consisting of *Echinacea*, soy/red clover, rosemary/lemon balm, cascara, barley grass, and *phyllanthus amarus/niruri*.

* * * * *